United States Patent
Marzi et al.

(10) Patent No.: US 7,851,621 B2
(45) Date of Patent: Dec. 14, 2010

(54) SYNTHESIS OF DEOXYBIOTINYL HEXAMETHYLENEDIAMINE-DOTA

(75) Inventors: Mauro Marzi, Rome (IT); Maria Di Marzo, Caserta (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 480 days.

(21) Appl. No.: 11/993,185

(22) PCT Filed: May 31, 2006

(86) PCT No.: PCT/EP2006/062800

§ 371 (c)(1),
(2), (4) Date: Feb. 19, 2008

(87) PCT Pub. No.: WO2007/003478

PCT Pub. Date: Jan. 11, 2007

(65) Prior Publication Data

US 2010/0184972 A1    Jul. 22, 2010

(30) Foreign Application Priority Data

Jun. 30, 2005    (IT) .......................... RM2005A0345

(51) Int. Cl.
*C07D 245/00* (2006.01)
(52) U.S. Cl. ...................................... 540/470
(58) Field of Classification Search ....................... None
See application file for complete search history.

(56) References Cited

U.S. PATENT DOCUMENTS

2005/0085630 A1    4/2005    Olejnik et al.

FOREIGN PATENT DOCUMENTS

WO    WO 02/066075    8/2002

OTHER PUBLICATIONS

Giuseppina Sabatino, et a., A New Biotin Derivative-Dota Conjugate as a Candidate . . . , J. Med. Chem. vol. 46, pp. 3170-3173, 2003.

*Primary Examiner*—James O. Wilson
*Assistant Examiner*—Noble Jarrell
(74) *Attorney, Agent, or Firm*—Lucas & Mercanti, LLP

(57) ABSTRACT

A process for the synthesis of deoxybiotinyl hexamethylenediamine0-DOTA is herein described. Said process comprises reacting biotinyl hexamithylenediamine with tri-t-butyl DOTA in the presence of benzotriazol-1-yl-oxytripyrrolidinophosphonium hexafluorophosphate, as the condensing agent, and triethylamine, as a base.

4 Claims, No Drawings

SYNTHESIS OF DEOXYBIOTINYL HEXAMETHYLENEDIAMINE-DOTA

FIELD OF THE INVENTION

The invention reported here relates to an improved procedure for the synthesis of deoxybiotinyl hexamethylenediamine-DOTA.

BACKGROUND OF THE INVENTION

The compound deoxybiotinyl hexamethylenediamine-DOTA has been described in international patent application WO 02066075 under the name of the Applicant. DOTA is 1,4,7,10-tetraazacyclododecanotetra-acetic acid (1,4,7,10-tetraazacyclododecanetetra-acetic acid).

The structural formula of deoxybiotinyl hexamethylenediamine-DOTA is reported here for completeness.

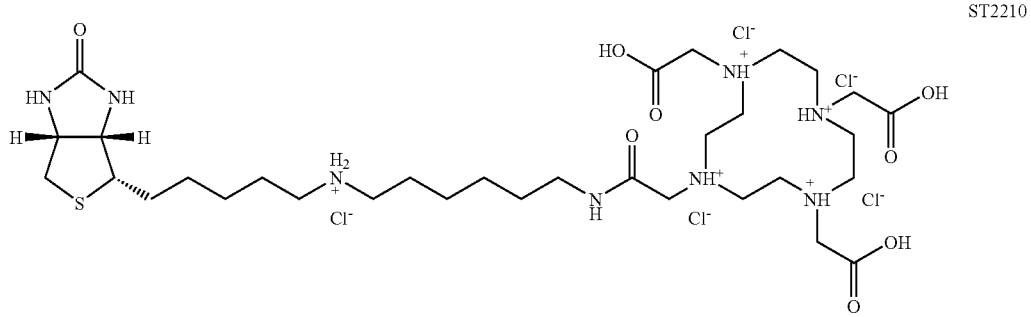

ST2210

The process for synthesising this product is also described in the same patent application WO 02066075 and also reported in the example on page 15 of the above-mentioned application. The compound reported here as ST2210 corresponds to compound 4 of the Example of WO 02066075. In particular the intermediate product biotinyl hexamethylenediamine hydrochloride (ST2551 or compound 3 of the example of WO 02066075), was obtained with preparatory chromatography with a yield of 55% and an undefined titre.

The final deoxybiotinyl hexamethylenediamine-DOTA product (ST2210 or compound 4 of the example of WO 02066075), was obtained by condensing ST2551 with DOTA as illustrated in diagram 1.

Diagram 1

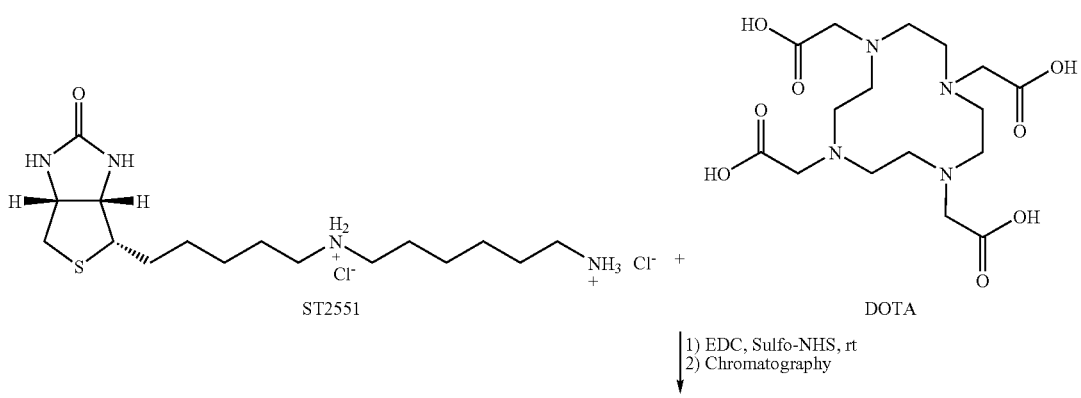

-continued

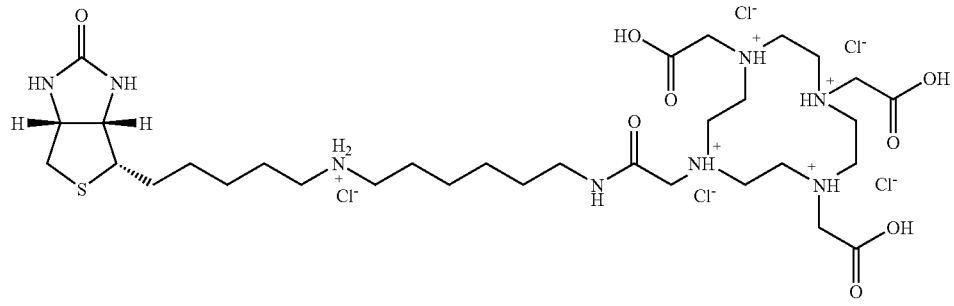

ST2210

The reaction conducted in this way produced low synthetic yields (the presence in DOTA of four unprotected carboxylic functionality equivalents, involved the formation of various by-products) and problems with purification. Indeed to obtain the end product it was necessary to use HPLC on a preparatory scale with a yield of 20%.

DESCRIPTION OF THE INVENTION

In the scale-up study, in order to improve the yield of the process and make the purification process easier, alternative synthesis methods were examined:

The improved synthesis process has the following advantages over the one described earlier:

1. in the coupling step or condensation (described in WO 02066075 as "step d") the use of tri-tert-butyl-DOTA avoids the formation of more condensation products, due to the partial reactivity of the free carboxyls, which occurred even when working under controlled pH conditions;
2. still in the same step, the condensing agent and the base were changed; the improved yield was obtained using benzotriazol-1-yl-oxytripyrrolidinophosphium hexafluorophosphate (PyBOP-Benzotriazol-1-yl-oxytripyrrolidinophosphonium hexafluorophosphate), as the condensing agent and triethylamine (TEA) as the base;
3. biotinyl hexamethylenediamine (ST2251) is used as a free base, having shown that the use of the dihydrochloride caused an increase in the quantity of unwanted products; in particular there was a noticeable formation of a by-product corresponding to the dimer, in which ST2551 reacts with 2 molecules of tri-t-butyl-DOTA;
4. the final step consists of the hydrolysis of the three ter-butyl groups in acid aqueous solution, for example using from 3N to 6N HCl in different ratios with the product for times ranging between 1 hour and 12 hours, with yields ranging between 96% and 98%;
5. elimination from the synthesis process of two rather laborious preparatory chromatography stages;
6. obtaining a product with a titre of from 94% to 96%.

Therefore the object of the present invention is a process for synthesising deoxybiotinyl hexamethylenediamine-DOTA which comprises reacting biotinyl hexamethylenediamine with tri-t-butyl-DOTA in the presence of benzotriazol-1-yl-oxytripyrrolidinophosphonium hexafluorophosphate, as the condensing agent, and triethylamine, as the base.

The process of the present invention therefore involves a step following the condensation step which is hydrolysis at acid pHs.

Condensation is preferably carried out in an organic solvent. More preferably this solvent is dichloromethane.

Of those analysed, the best synthesis method developed is the one which involved the stages illustrated in diagram 2.

In addition, the invention is illustrated with Examples which are in no way limited to the invention itself.

Diagram 2

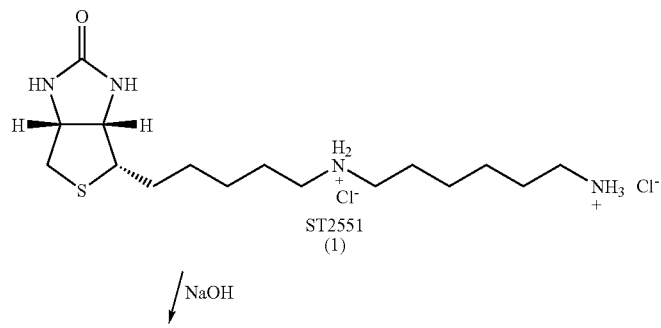

ST2551
(1)

↓ NaOH

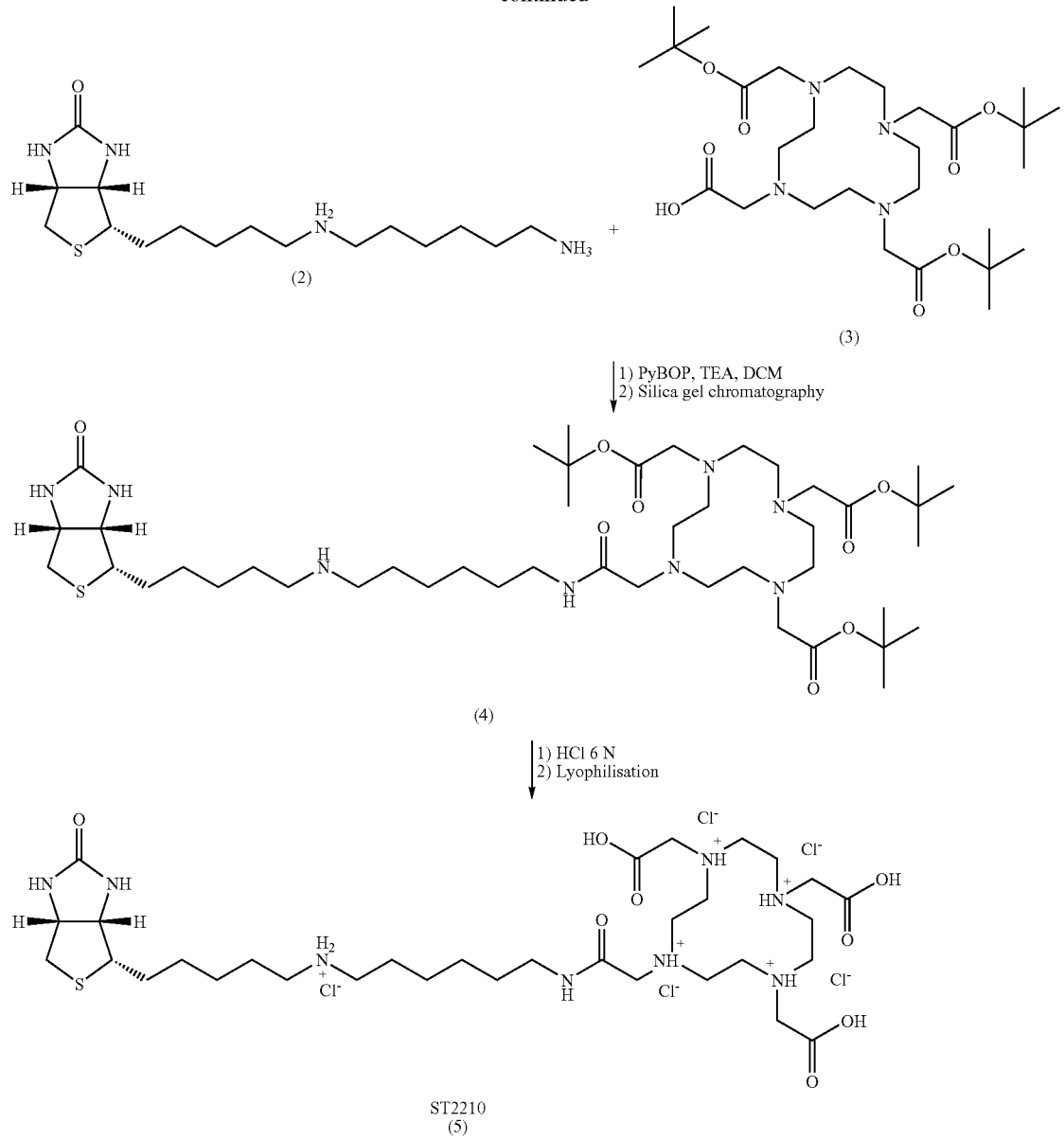

ST2210
(5)

EXAMPLES

For the Numbering of the Compounds Refer to Diagram 2

Methods

The tests carried out were monitored using an analytical HPLC system connected to a diode array detector and to a mass spectrometer with an electrospray. The analytical method developed involves the use of an ACE C-18 analytical column (150×4.60 mm, 5μ), a flow rate of 1.0 mL/min and a linear elution gradient of 5-95% of B in 20 min (A=$H_2O$+ 0.1% TFA; B=AcCN+0.1% TFA), or 10-90% of B in 20 min, or alternatively a 10% isocratic solution of B for 6 min, followed by the gradient 10-90% of B in 20 min. For the end product ST2210, a method working in an isocratic solution of B at 15% is used for 40 min. The range of wave lengths examined by the detector is 205-400 nm.

Rapid monitoring by TLC involves the use of eluents mixtures of the OEt acid type:isopropanol:$NH_3$ 30% or DCM: isopropanol:$NH_3$ 30% (4:5:1), revealing the products sorted out (not UV visible) by means of $I_2$ or phosphomolybdic reagent.

Preparation of biotinyl hexamethylenediamine (ST2551) as the Free Base (2.)

Product ST2551 [(1), purity of 91%, 400 mg, 1.0 mmol) was dissolved in water (20 mL) and the solution was put into a separating funnel; a solution of NaOH 2M (20 mL) was added and the product precipitated was extracted with DCM (40 mL) three times. The combined organic phases were dehydrated with anhydrous $Na_2SO_4$ and evaporated under reduced pressure. The product was obtained (2) as a white solid (290 mg, yield=98%).

$^1$H-NMR (200 MHz, $CDCl_3$) δ (ppm): 1.25-2.05 [m, 16H, $CH(CH_2)_4$ and $NHCH_2(CH_2)_4)$]; 2.50-3.30 (m, 9H, 2×HCHS and CHS and 3×$CH_2N$); 4.32 (m, 1H, CHCHNH); 4.51 (m, 1H, CHCHNH); 5.77 (s, 1H, CONH); 6.05 (s, 1H, CONH).

ES-MS m/z: 329.5 $[M+H]^+$.

Synthesis of deoxybiotinyl hexamethylenediamine—ter-butyl-DOTA (4)

A solution of tri-tert-butyl-DOTA [(3), 524 mg, 0.915 mmol, 1 eq], PyBOP (714 mg, 1.37 mmol, 1.5 eq) and triethylamine (166 μL, 1.19 mmol, 1.3 eq) in DCM (5 mL) left under agitation at room temperature for 10 minutes, was added drop by drop to a solution of ST2551-free base [(2), 300 mg, 0.915 mmol, 1 eq) in DCM (5 mL), obtained by heating the mixture at 40° C. for 5 min. It was left to react at room temperature for 3 hours, monitoring the completeness of the reaction by TLC and LC-MS, according to the methods above.

At the end of the reaction the solvent was evaporated under reduced pressure, the residue was dissolved in DCM and was washed twice with NaOH 1M. The organic phase was dehydrated on $Na_2SO_4$ and evaporated under vacuum. The residue thus obtained underwent chromatography on a silica gel column (ratio in weight of crude product:silica 1:30), using as the eluent system a DCM mixture:isopropanol 5:4 to which is added an increasing concentration of 30% aqueous $NH_3$ (from 0.2 to 1). The column was packed with the initial DCM mixture:isopropanol:$NH_3$ (5:4:0.2) and the process was continued with the gradient of $NH_3$. [the eluent mixture usually becomes homogeneous after agitation; only in the final phase of the elution, with $NH_3$=1 it may prove to be necessary to add isopropanol to improve miscibility, in this case using the volumetric ratio (4:5:1) (DCM:isopropanol:$NH_3$). A slightly yellow oily product was obtained which tended to produce a foamy solid under vacuum [(4), 600 mg, yield=74%).

$^1$H-NMR (300 MHz, DMSO-$d_6$, T=50° C.) δ (ppm): 1.16-1.70 (m, 43H, $CH(CH_2)_4$ and $NHCH_2(CH_2)_4$ and 9×$CH_3$); 2.40-3.32 (m, 34H, 2×HCHS and 3×$CH_2N$, 8×DOTA-ring $CH_2$ and CHS and 4×DOTA $CH_2CO$ and NH amine); 4.13 (m, 1H, CHCHNH); 4.29 (m, 1H, CHCHNH); 6.18 (s, 1H, NH biotin); 6.21 (s, 1H, NH biotin); 8.10 (t, 1H, NH amide).

$^{13}$C-NMR (75 MHz, DMSO-$d_6$) δ (ppm): 27.22; 27.35; 27.56; 28.50; 28.61; 29.04; 29.23; 30.14; 30.25; 30.39; 39.14; 40.42; 50.07; 52.59; 52.82; 53.24; 54.72; 56.14; 56.92; 57.38; 59.31; 60.05; 61.90; 80.75; 163.34; 170.98; 171.25.

ES-MS m/z: 883.4 $[M+H]^+$.

Synthesis of deoxybiotinyl hexamethylenediamine-DOTA [ST2210, (5)]

A solution of (4) (210 mg, 0.238 mmol) in HCl 6N [1 mL, 20% w/v solution of (4)] was left under agitation at room temperature for 1 hour. Then the mixture was evaporated at reduced pressure, the residue was dissolved in $H_2O$ (approx. 1:50 w/v) and the solution was subjected to lyophilisation. A white solid was obtained (205 mg, 96%). $^1$H-NMR (200 MHz, DMSO-$d_6$) δ (ppm): 1.30-1.77 [m, 16H, $CH(CH_2)_4$ and $NHCH_2(CH_2)_4$]; 2.59 (d, 1H, HCHS); 2.77-2.88 (m, 7H, HCHS and 3×$CH_2N$); 2.98-3.70 (m, 25H, 8×DOTA-ring $CH_2$ and CHS and 4×DOTA $CH_2CO$); 4.15 (m, 1H, CHCHNH); 4.31 (m, 1H, CHCHNH); 7.58 (br s, 2H, 2×biotin NH); 8.86 (t, 1H, NH amide); 9.19 (br s, 2H, $NH_2^+$).

$^{13}$C-NMR (75 MHz, DMSO-$d_6$) δ (ppm): 25.77; 25.85; 26.32; 26.53; 26.70; 28.74; 29.16; 47.08; 47.16; 48.54; 49.00; 51.35; 53.13; 54.51; 55.38; 56.02; 59.90; 61.61; 163.44; 165.58; 168.90; 172.31.

ES-MS m/z: 715.4 $[M+H]^+$.

The invention claimed is:

1. Process for synthesising deoxybiotinyl hexamethylenediamine-DOTA comprising reacting biotinyl hexamethylenediamine with tri-t-butyl-DOTA in the presence of benzotriazol-1-yl-oxytripyrrolidinophosphonium hexafluorophosphate, as the condensing agent, and triethylamine, as the base.

2. Process according to claim 1, in which biotinyl hexamethylenediamine is reacted with tri-t-butyl-DOTA in an organic solvent.

3. Process according to claim 2 in which the organic solvent is dichloromethane.

4. Process according to claim 1, involving a subsequent step of hydrolysis in an aqueous environment with an acid pH.

* * * * *